US006300433B1

(12) United States Patent
Rodriguez et al.

(10) Patent No.: US 6,300,433 B1
(45) Date of Patent: Oct. 9, 2001

(54) OLEFIN COPOLYMERIZATION PROCESS WITH BRIDGED HAFNOCENES

(75) Inventors: George Rodriguez, Houston; Donna J. Crowther, Seabrook, both of TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/422,533

(22) Filed: Oct. 21, 1999

Related U.S. Application Data

(60) Provisional application No. 60/105,329, filed on Oct. 23, 1998.

(51) Int. Cl.$^7$ .......................................................... C08F 4/52
(52) U.S. Cl. .......................... 526/127; 526/78; 526/128; 526/131; 526/348.2; 526/348.5; 526/348.6
(58) Field of Search .............................. 526/127, 78, 128, 526/131, 348.2, 348.5, 348.6

(56) References Cited

U.S. PATENT DOCUMENTS

| 5,198,401 | 3/1993 | Turner et al. . |
| 5,324,800 | 6/1994 | Welborn, Jr. et al. . |
| 5,408,017 | 4/1995 | Turner et al. . |
| 5,767,208 | 6/1998 | Turner et al. . |

FOREIGN PATENT DOCUMENTS

| 0612768 | * | 8/1994 | (EP) . |
| 0 612 768 B1 | | 8/1994 | (EP) . |
| 0 786 466 A1 | | 7/1997 | (EP) . |
| 0 824 113 A1 | | 2/1998 | (EP) . |
| WO 96/28480 | | 9/1996 | (WO) . |
| WO 96/33227 | | 10/1996 | (WO) . |
| WO 97/29845 | | 8/1997 | (WO) . |
| WO-99/45040 | * | 9/1999 | (WO) . |
| WO 99/45050 | | 9/1999 | (WO) . |

OTHER PUBLICATIONS

"Novel transition metal compounds for polymerization of olefins with improved efficiency and polymerization of olefins using them", Inoe, Norihide, et al, Chemical Abstracts, vol. 24, No. 14, (Apr. 1, 1996), Abstract No. 177218 and JP 07 247309–Abstract.

"Metallocenes", TOSOH Corp., Polymerization, pp. 441–462, (1995).

"Synthesis amd Applications of Metallocene–Based Elastomers", Miyata, et al, TOSOH Corp., (1996).

"Ethene/propene copolymerisation by [Me$_2$C(3–RCp)(Flu)]ZrCl$_2$/MAO (R = H,Me, $^{iso}$Pr,$^{tert}$Bu)", Arndt, et al, Macromol. Chem. Phys., vol. 199, 1135–1152, (1998).

"Ethylene/1–hexene copolymerization with Ph$_2$C(Cp)9Flu)ZrCl$_2$ derivatives: correlation between ligand structure and copolymerization behavior at high temperature", Yano, et al, Macromol. Chem. Phys., vol. 200, pp. 1542–1553, (1999).

* cited by examiner

Primary Examiner—David W. Wu
Assistant Examiner—William Cheung
(74) Attorney, Agent, or Firm—William G. Muller; Charles E. Runyan

(57) ABSTRACT

The invention is directed to olefin polymerization processes using bridged hafnocene catalyst complexes that are surprisingly stable under high temperature olefin polymerization processes such that olefin copolymers can be prepared with high molecular weights and catalyst activities. More specifically, the invention is a polymerization process for ethylene copolymers having a melt index of about 0.850 to about 0.930 comprising contacting, under homogeneous polymerization conditions at a reaction temperature at or above 60° C. to 250° C., ethylene and one or more comonomers capable of insertion polymerization with a bridged hafnocene catalyst complex derived from A) a biscyclopentadienyl hafnium organometallic compound having i) at least one unsubstituted cyclopentadienyl ligand or aromatic fused-ring substituted cyclopentadienyl ligand, ii) one aromatic fused-ring substituted cyclopentadienyl ligand, iii) and a covalent bridge connecting the two cyclopentadienyl ligands, said bridge comprising a single carbon or silicon atom with two aryl groups, each substituted with a $C_1$–$C_{20}$ hydrocarbyl or hydrocarbylsilyl group at least one of which is a linear $C_3$ or greater substitutent; and B) an activating cocatalyst.

20 Claims, No Drawings

OLEFIN COPOLYMERIZATION PROCESS WITH BRIDGED HAFNOCENES

CROSS-REFERENCES TO RELATED APPLICATIONS

This provisional application is related to the earlier filed provisional application No. 60/105,329 filed Oct. 23, 1998.

TECHNICAL FIELD

This invention relates to olefin copolymerization processes using substituted hafnocene catalyst compounds with noncoordinating anions.

BACKGROUND ART

Olefin polymers comprising ethylene and at least one or more α-olefin and optionally one or more diolefin make up a large segment of polyolefin polymers and will be addressed as "ethylene copolymers" herein. Such polymers range from crystalline polyethylene copolymers to largely amorphous elastomers, with a new area of semi-crystalline "plastomers" in between. In particular, ethylene copolymer plastomers are now a well established class of industrial polymers having a variety of uses associated with their unique properties, such as elastomeric properties and their thermo-oxidative stability. Uses of the plastomers include general thermoplastic olefins, films, wire and cable coatings, polymer modification (by inclusion in blends with other polyolefins), injection molding, foams, footwear, sheeting, functionalized polymers (such as by free-radical graft addition of polar monomers) and components in adhesive and sealant compounds.

Commercially prepared ethylene copolymers have been traditionally been made via Ziegler-Natta polymerization with catalyst systems largely based on vanadium or titanium. Newer metallocene catalyst compounds have received attention due to their ease of larger monomer incorporation and potential increases in polymerization activities. U.S. Pat. No. 5,324,800 describes metallocenes having substituted and unsubstituted cyclopentadienyl ligands which are suitable for producing high molecular weight olefin polymers, including linear, low density copolymers of ethylene with minor amounts of α-olefin.

Noncoordinating anions useful as catalyst components with such metallocenes is known. The term "noncoordinating anion" is now accepted terminology in the field of olefin polymerization, both by coordination or insertion polymerization and carbocationic polymerization. The noncoordinating anions function as electronic stabilizing cocatalysts, or counterions, for cationic metallocenes which are active for olefin polymerization. The term "noncoordinating anion" as used here and in the references applies both to noncoordinating anions and weakly coordinating anions that are not so strongly coordinated to the cationic complex as so to be labile to replacement by olefinically or acetylenically unsaturated monomers at the insertion site. U.S. Pat. No. 5,198, 401 describes a preferred noncoordinating anion tetra (perflourophenyl) boron, [B(pfp)$_4$]-or [B(C$_6$F$_5$)$_4$]-, wherein the perfluorinated phenyl ligands on the boron makes the counterion labile and stable to potential adverse reactions with the metal cation complexes.

The utility of metallocene-based ionic catalysts in high temperature olefin polymerization is described in U.S. Pat. Nos. 5,408,017 and 5,767,208, EP 0 612 768, and WO 96/33227. Each addresses suitable metallocene catalysts for high temperature processes for olefin copolymerization. High molecular weight ethylene/α-olefin copolymers is an objective of EP 0 612 768 and is addressed with catalyst systems based on bis(cyclopentadienyl/indenyl/fluorenyl) hafnocenes which are combined with an alkyl aluminum compound and an ionizing ionic compound providing a non-coordinating anion.

As described above, a recognized problem for high temperature polymerization, particularly where significant content of comonomer incorporation in ethylene copolymers is to be sought, is an observed decrease in molecular weight, or increase in melt index (MI). Means of maintaining high molecular weights, or low M.I., in ethylene copolymers of low density (high comonomer content) while operating at economically preferable high polymerization reaction temperatures and high polymer production rates is highly desirable.

BRIEF SUMMARY OF THE INVENTION

The invention thus addresses specifically substituted, bridged hafnocene catalyst complexes comprising noncoordinating anions that are surprisingly stable under high temperature olefin polymerization processes such that olefin copolymers with high molecular weights can be prepared at surprisingly high production rates. More specifically, the invention relates to a polymerization process for ethylene copolymers having a density of about 0.850 to about 0.930 comprising contacting, under supercritical or solution polymerization conditions at a reaction temperature at, or above, 60° C. to 225° C., or below, ethylene and one or more comonomers capable of insertion polymerization with a hafnocene catalyst complex derived from A) a biscyclopentadienyl hafnium organometallic compound having i) at least one unsubstituted cyclopentadienyl ligand or aromatic fused-ring substituted cyclopentadienyl ligand not having additional substitutents on said ligand, ii) one substituted or unsubstituted, aromatic fused-ring substituted cyclopentadienyl ligand, and iii) a covalent bridge connecting the two cyclopentadienyl ligands, said bridge comprising a single carbon or silicon atom with two aryl groups, each substituted with a C$_1$–C$_{20}$ hydrocarbyl or hydrocarbylsilyl group at least one of which is a linear C$_3$ or greater substitutent; and B) an activating cocatalyst, preferably a precursor ionic compound comprising a halogenated tetraaryl-substituted Group 13 anion.

DETAILED DESCRIPTION OF THE INVENTION

The bridged hafnium compounds of the invention include those having a single substituted carbon or silicon atom bridging two cyclopentadienyl-containing (Cp) ligands of the hafnium metal centers (iii), the aromatic fused-ring substituted cyclopentadienyl ligand or ligands, preferably those containing C$_1$–C$_{30}$ hydrocarbyl or hydrocarbylsilyl substituents on the ii) non-cyclopentadienyl aromatic ring. The bridge substituents preferably comprise C$_1$–C$_{20}$ linear or branched alkyl, or C$_1$–C$_{20}$ substituted-silyl, substituted phenyl groups, the alkyl or substituted-silyl substituents located in the para- or meta-positions of the aryl groups, preferably wherein at least one of said alkyl substituents is a C$_3$ or higher linear n-alkyl substitutent, preferably C$_4$ or higher. Specific examples include methyl, ethyl, n-propyl, n-butyl, sec-butyl, isobutyl, tert-butyl, n-pentyl, neopentyl, etc. Substituents present on the non-cyclopentadienyl aromatic rings of the aromatic fused-ring substituted cyclopentadienyl li,and (ii), such inclusive of indenyl and fluorenyl derivatives of cyclopentadienyl groups, typically include one or more $C_1$ to $C_{30}$ hydrocarbon or hydrocarbylsilyl groups selected from linear, branched, cyclic, aliphatic, aromatic or combined structure groups, including fused-ring or pendant configurations. Examples include methyl, isopropyl, n-propyl, n-butyl, isobutyl, tertiary butyl, neopentyl, phenyl, n-hexyl, cyclohexyl, and benzyl. For the purposes of this application the term "hydrocarbon" or "hydrocarbyl" is meant to include those compounds or groups that have essentially hydrocarbon characteristics but optionally contain not more than about 10 mol.% non-carbon atoms, such as boron, silicon, oxygen, nitrogen, sulfur and phosphorous. "Hydrocarbylsilyl" is exemplified by, but not limited to, dialkyl- and trialkylsilyls. Similarly the use of hetero-atom containing cyclopentadienyl rings or fused rings, where a non-carbon Group 14, 15 or 16 atom replaces one of the ring carbons in the Cp ring or in a ring fused thereto, is considered for this specification to be within the terms "cyclopentadienyl", "indenyl", and "fluorenyl". See, for example, the teachings of WO 98/37106, having common priority with U.S. Ser. No. 08/999,214, filed 12/29/97, pending and WO 98/41530, having common priority with U.S. Ser. No. 09/042,378, filed Mar. 13, 1998, abandoned incorporated by reference for purposes of U.S. patent practice.

Specific bridged hafnium catalysts innclude those derived from: (1) indenyl-based complexes such as the isomers, or mixtures, of (para-n-butylphenyl) (para-t-butylphenyl) methylene (fluorenyl) (indenyl) hafnium dimethyl, (para-n-propylphenyl)(para-methylphenyl)methylene (fluorenyl) (indenyl) hafnium dimethyl, di(para-n-butylphenyl) methylene (2,7-di tertbutyl fluorenyl) (indenyl) hafnium dimethyl, (para-n-butylphenyl)(para-t-butylphenyl) methylene (2,7-di tertbutyl fluorenyl) (indenyl) hafnium dimethyl, (para-n-butylphenyl)(para-t-butylphenyl) methylene (2,7-dimethyl fluorenyl)(indenyl) hafnium dibenzyl and di(para-n-butylphenyl) methylene (fluorenyl) (indenyl) hafnium dimethyl; and, (2) fluorenyl-based complexes such as (para-n-propylphenyl)(para-i-propylphenyl) silyl (fluorenyl) (fluorenyl) hafnium di-t-butyl, di(para-n-propyl phenyl)methyl ene (2,7-di-tert-butyl-5-methylfluorenyl) (fluorenyl) hafnium dimethyl; and (3) cyclopentadienyl-based complexes such as the isomers, or mixtures, of (para-n-propylphenyl)(para-i-propylphenyl) methylene (fluorenyl) (cyclopentadienyl) hafnium dimethyl, (para-n-butylphenyl)(para-t-butylphenyl)methylene (fluorenyl) (cyclopentadienyl) hafnium dimethyl, di(para-n-butylphenyl)methylene (2,7-di tertbutyl fluorenyl) (cyclopentadienyl) hafnium dimethyl, (para-n-butylphenyl) (para-t-butylphenyl)methylene (2,7-di tertbutyl fluorenyl) (cyclopentadienyl) hafnium dimethyl, and di(para-n-butylphenyl)methylene (2,7-dimethyl fluorenyl) (cyclopentadienyl) hafnium dimethyl or dibenzyl. It has been found that the substituted bridge-containing compounds, such as those asymmetric compounds listed above, are particularly useful in accordance with the invention.

In particular, for the bridged hafnium compounds, increasing the degree of substitution on the aromatic fused-ring substituted ligand (ii) is effective for increased molecular weight, as is the use of the invention covalent bridge (iii) between the cyclopentadienyl ligands as described above. The substituted aryl groups of the bridging atom contribute to surprisingly increased activity, or productivity of the catalyst, as compared to the simpler diaryl substituted analogs, without detrimental effect on the molecular weight of the resulting copolymers. Preferably substitution on fluorenyl or indenyl radicals (ii) in the hafnium compounds will generally comprise two or more $C_1$ to $C_{30}$ hydrocarbyl or hydrocarbylsilyl substituents for a ring hydrogen of at least one 6-member fused-ring, preferably both where fluorenyl.

The invention activating cocatalyst, precursor ionizing compounds comprise Group 13 element complexes having at least two halogenated aromatic ligands such as the halogenated tetraphenyl boron and aluminum compounds exemplified in the identified prior art. Preferred aromatic ligands consist of polycyclic aromatic hydrocarbons and aromatic ring assemblies in which two or more rings (or fused ring systems) are joined directly to one another or together. These ligands, which may be the same or different, are covalently bonded directly to the metal/metalloid center. In a preferred embodiment the aryl groups are halogenated tetraaryl Group 13 element anionic complexes comprising at least one fused polycyclic aromatic hydrocarbon or pendant aromatic ring. Indenyl, napthyl, anthracyl, heptalenyl and biphenyl ligands are exemplary. Thus, for example, suitable ligands include those illustrated below, the open bond being to the Group 13 atom. See also the polycyclic compound examples in the literature for additional ligand selection, e.g., Nomenclature of Organic Compounds, Chs. 4–5 (ACS, 1974).

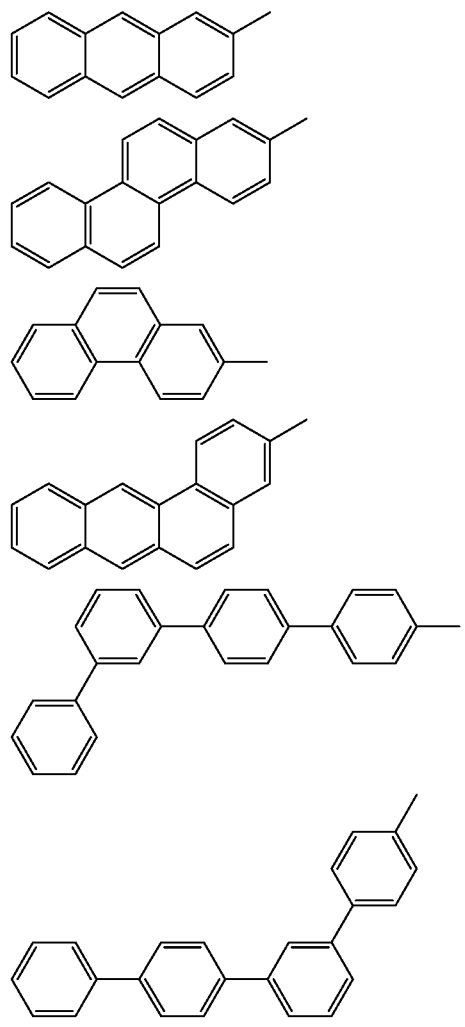

I

-continued

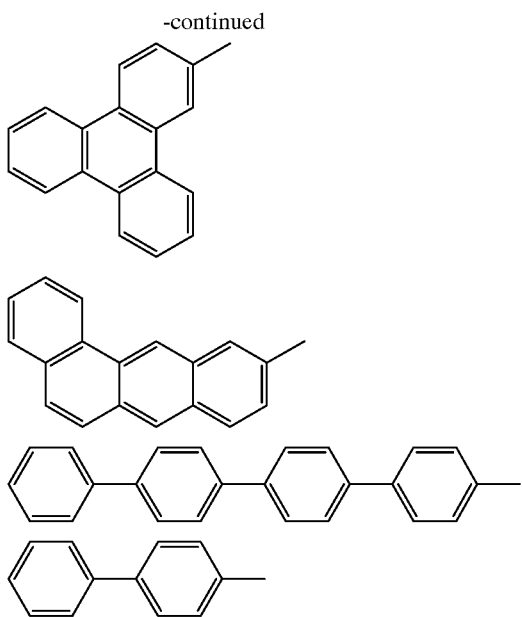

These preferred ionizing compounds comprise salts of anions comprising ligands capable of a tetrahedral orientation. Thus those ligands structurally compatible with each other in the sense of being bonded to the Group 13 metal center without hindering the bonding of additional halogenated, aryl ligands thereto are preferred. Examples include those having pendant aryl groups at the para- or meta-position of the aryl ring closest to the metal/metalloid center, and those having fused aryl groups bonded to the aryl ring closest to the metal/metalloid center at the 2-, 3- or 3-,4- positions. See Table I above. Those anions with mixed ligands are also suitable. Tris(perfluorophenyl)(perfluoronapthyl) borate is an illustrative complex. Thus, generically speaking, the Group 13 complexes useful in a accordance with the invention will typically conform to the following formula:

$$[M(A)_{4-n}(C)_n]^-$$

where, M is a Group 13 element, A is an nonhindering ligand as described above, C is a hindering ligand, one having bulky substitutents on the closest aryl ring bonded to the metal/metalloid center other than those described as suitable above, and n=0, 1, or 2. See also copending application U.S. Ser. No. 60/087447, filed Jun. 1, 1998, U.S. Pat. No. 4,223,371 filed Sep. 16, 1980 and its equivalent WO 99/45042, the teachings of which are referred to and incorporated by reference for purposes of U.S. patent practice.

For both fused aromatic rings and aromatic ring assemblies, the halogenation is highly preferred so as to allow for increased charge dispersion that contributes along with steric bulk as independent features decreasing the likelihood of ligand abstraction by the strongly Lewis acidic metallocene cation formed in the catalyst activation. Additionally, halogenation inhibits reaction of the hafnium cation with any remaining carbon-hydrogen bonds of the aromatic rings, and perhalogenation precludes such potential undesirable reactions. Thus it is preferred that at least one third of hydrogen atoms on carbon atoms of the aryl ligands can be replaced by halogen atoms, and more preferred that the aryl ligands be perhalogenated. Fluorine is the most preferred halogen, perfluorinated aryl ligands are most preferred.

Means of preparing ionic catalyst systems comprising catalytically active cations of the hafnium compounds and suitable noncoordinating anions are conventionally known, see for example U.S. Pat. No. 5,198,401, WO 92/00333, WO 97/22639, and EP 0 612 768. Typically the methods comprise obtaining from commercial sources or synthesizing the selected transition metal compounds comprising an abstractable ligand, e.g., hydride, halide, alkyl, alkenyl or hydro-carbyl-silyl group, and contacting them with a noncoordinating anion source or suitable precursor compounds in a suitable solvent. The anion precursor compound abstracts a monoanionic ligand (or one monoanionic bond of bidentale alkenyl ligands) that completes the valency requirements of the preferred hafnium metallocene compounds. The abstraction leaves the hafnocenes in an essentially cationic state which is counterbalanced by the stable, compatible and bulky, noncoordinating anions according to the invention. Each of the documents of this paragraph are incorporated by reference for purposes of U.S. patent practice.

The noncoordinating anions are preferably introduced into the catalyst preparation step as ionic compounds having an essentially cationic complex which abstracts a non-cyclopentadienyl, labile ligand of the transition metal compounds which upon abstraction of the non-cyclopentadienyl ligand, leave as a by-product the noncoordinating anion portion. Hafnium compounds having labile hydride, alkyl, or silyl ligands on the metal center are highly preferred for the ionic catalyst systems of this invention since known in situ alkylation processes may result in competing reactions and interactions that tend to interfere with the overall polymerization efficiency under high temperature conditions in accordance with the preferred process embodiments of the invention.

Suitable cations for precursor compounds capable of providing the noncoordinating anions of the invention cocatalysts include those known in the art. Such include the nitrogen-containing cations such as those in U.S. Pat. No. 5,198,401, the carbenium, oxonium or sulfonium cations of U.S. Pat. No. 5,387,568, metal cations, e.g., Ag+ or Li+, the silylium cations of WO 96/08519, and the hydrated salts of Group 1 or 2 metal cations of WO 97/22635.

Examples of preferred precursor salts of the noncoordinating anions capable of ionic cationization of the metallocene compounds of the invention, and consequent stabilization with a resulting noncoordinating anion include trialkyl-substituted ammonium salts such as triethylammonium tetrakis(perfluoronapthyl) or tetrakis(perfluoro-4-biphenyl)boron, tri(n-butyl)ammonium tetrakis (perfluoronapthyl) or tetrakis(perfluoro-4-biphenyl)boron, tri(n-octyl)ammonium tetrakis(perfluoronapthyl) or tetrakis(perfluoro-4-b iphenyl)boron, trim ethylammonium tetrakis (perfluoronapthyl) or tetrakis(perfluoro-4-biphenyl)boron, trimethylammonium tetra tetrakis(perfluoronapthyl) or tetrakis(perfluoro-4-biphenyl)boron, tributylammonium tetrakis(perfluoronapthyl) or tetrakis(perfluoro-4-biphenyl) boron, tripropylammonium tetrakis(perfluoronapthyl) or tetrakis(perfluoro-4-biphenyl), tributylammonium tetrakis (perfluoronapthyl) or tetrakis(perfluoro-4-biphenyl)boron, tributylammonium tetrakis(perfluoronapthyl) or tetrakis (perfluoro-4-biphenyl)boron, tributylammonium tetrakis (perfluoronapthyl) or tetrakis(perfluoro-4-biphenyl)boron, tri(n-butyl)ammonium tetrakis(perfluoronapthyl) or tetrakis (perfluoro-4-biphenyl)boron and the like; N,N-dialkyl anilinium salts such as N,N-dimethylanilinium tetrakis (perfluoronapthyl) or tetrakis(perfluoro-4-biphenyl)boron, N,N-di(n-dodecyl )ani Ii nium tetrakis(perfluoronapthyl) or tetrakis(perfluoro-4-biphenyl)boron, N,N-2,4,6-pentamethylanium tetrakis(perfluoronapthyl) or tetrakis(perfluoro-4-biphenyl)boron and the like; dialkyl ammonium salts such as di-(n-dodecyl)ammonium tetrakis(perfluoronapthyl) or tetrakis(perfluoro-4-biphenyl)boron, dicyclohexylammonium tetrakis(perfluoronapthyl) or tetrakis(perfluoro-4-biphenyl)boron and the like; and triaryl phosphonium salts such as triphenylphosphonium tetrakis(perfluoronapthyl) or tetrakis(perfluoro-4-biphenyl)boron, tri(methylphenyl)phosphonium tetrakis (per-fluoronapthyl) or tetrakis(perfluoro-4-biphenyl)boron, tri(dimethylphenyl)phosphonium tetrakis(perfluoronapthyl) or tetrakis(perfluoro-4-biphenyl)boron and the like. See also the long chain group-containing nitrogen Lewis acid complexes (e.g., of protonated ammonium salts) of WO 97/35983, the catalyst activators of which are suitable in accordance with this invention and the teachings of which is incorporated by reference for purposes of U.S. prosecution.

Further examples of suitable anionic precursors include those comprising a stable carbenium ion, and a compatible non-coordinating anion. These include tropillium tetrakis(perfluoronapthyl) or tetrakis(perfluoro-4-biphenyl) borate, triphenylmethylium tetrakis(perfluoronapthyl) or tetrakis(perfluoro-4-biphenyl) borate, benzene (diazonium) tetrakis(perfluoronapthyl) or tetrakis(perfluoro-4-biphenyl) borate, tropillium tetrakis(perfluoronapthyl) or tetrakis(perfluoro-4-biphenyl)borate, triphenylmethylium tetrakis(perfluoronapthyl) or tetrakis(perfluoro-4-biphenyl)borate, benzene (diazonium) tetrakis(perfluoronapthyl) or tetrakis(perfluoro-4-biphenyl) borate, tropillium tetrakis(perfluoronapthyl) or tetrakis(perfluoro-4-biphenyl)borate, triphenylmethylium tetrakis(perfluoronapthyl) or tetrakis(perfluoro-4-biphenyl)borate, benzene (diazonium) tetrakis(perfluoronapthyl) or tetrakis(perfluoro-4-biphenyl)borate. The essentially structurally equivalent silylium borate or aluminate salts are similarly suitable.

The term "scavenver" as used in this application is used in its art-recognized sense of being sufficiently Lewis acidic to coordinate with polar contaminates and impurities adventiously occurring in the polymerization feedstreams or reaction medium. Such impurities can be inadvertently introduced with any of the polymerization reaction components, particularly with solvent, monomer and catalyst feed, and adversely affect catalyst activity and stability. In particular, for processes utilizing recycle streams of unconverted monomer for reprocessing, the necessity to use polar compounds as catalyst deactivators, or "killers", such as water or lower alcohols, effectively necessitates the use of scavengers, as does the natural occurrence of polar impurities in monomer feedstreams. It can result in decreasing or even elimination of catalytic activity, particularly when a metallocene cation-noncoordinating anion pair is the catalyst system. The polar impurities, or catalyst poisons include water, oxygen, metal impurities, etc. Preferably steps are taken before provision of such into the reaction vessel, for example by chemical treatment or careful separation techniques after or during the synthesis or preparation of the various components, but some minor amounts of scavenging compound will still normally be required in the polymerization process itself Typically the scavenging compound will be an organometallic compound such as the Group-13 organometallic compounds of U.S. Pat. No. 5,241,025, EP-A-0 426 638 and those of U.S. Pat. No. 5,767,208. Exemplary compounds include triethyl aluminum, triethyl borane, tri-isobutyl aluminum, methylalumoxane, isobutyl aluminumoxane, tri-n-hexyl aluminum and tri-n-octyl aluminum, those having bulky substituents covalently bound to the metal or metalloid center being preferred to minimize adverse interaction with the active catalyst. Addition of excess scavenger causes lower productivity, molecular weight and comonomer incorporation. The aluminum to hafnium molar ratios (Al:Hf) should accordingly be less than about 100:1, preferably less than about 75:1, more preferably less than about 50:1, and most preferably less than about 30:1. Molar ratios of less than 20:1 and less than 15:1 have been observed to be sufficient for the continuous processes described in this application.

The preferred scavenger is a long chain, linear tri-alkyl aluminum compound, and that longer chains are preferred over shorter chains. See WO 97/22635 and U.S. Pat. No. 5,767,208 for further discussion, this document is incorporated by reference for purposes of U.S. patent practice. Non-limiting examples of effective long chain, linear tri-alkyl ligand-containing scavengers include those comprised in the group defined by the formula M'R'R"R"', where M' is Al, and each of the R groups independently is a $C_4$ or higher linear, branched or cyclic alkyl group, preferably $C_6$ or higher, most preferably $C_8$ or higher. The long chain, linear alkyl aluminums where each alkyl substituent was of a length of $C_8$ or higher, preferably $C_9$ and higher were observed to exhibit optimal performance, that defined as having the least deleterious effect when used at a level in excess of the optimum level as described in the following paragraph. Specifically included are: tri-n-octyl aluminum, tri-n-decyl aluminum, tri-n-dodecyl aluminum, tri-n-hexadecyl aluminum, and the higher carbon number equivalents, e.g., $(C_{20})_3Al$, including those with mixed ligation, and mixed scavenger compounds as well. The hydrolyzed derivatives of these alkyl-ligand containing organoaluminum compounds will additionally be suitable. Additionally, it will be apparent that those scavenging compounds comprising both long-chain, linear and bulky ligands or mixed linear ligands, each ligand as described above, will also be suitable, but perhaps less desirable due to more involved or expensive syntheses.

A preferred polymerization process is that designed or conducted such that the cocatalyst components, that is the transition metal compounds and the anion precursor compounds, are maintained separately until just prior to or during polymerization use in the chosen reactor or reactors. An example is the use of dual injection of each catalyst component directly into the reactor or the use of T- or multi-joint mixing chambers just prior to injection into the reactor. Additional optimization can be achieved when the scavenger compound is introduced into the reactor independently of the catalyst system or compounds, preferably after the activation of the hafnocenes with the anion precursor cocatalysts.

The process of the invention is applicable to high pressure homogeneous polymerization, preferably employing less than 30 wt % of solvent, which is substantially adiabatic and where the heat of polymerization is accommodated by a rise in temperature of the reactor contents instead of internal or external cooling. In this case, the contents consist principally of unreacted monomer. Such process may be performed, under a single or dual phase homogeneous conditions at pressures from 250 to 3000 bar, preferably from 500 to 2500 bar, with or without unreactive diluents or solvents at temperatures generally above the melting point of the polymer being produced. Such processes are industrially known and may include the use of scavenger compounds and catalyst deactivation or killing steps, see for example U.S. Pat. No. 5,408,017, WO 95/07941, and WO 92/14766. Each of these documents and their U.S. counterparts are incorporated by reference for purposes of U.S. patent practice. Preferred catalyst deactivators, or killers, include high molecular weight, non-recyclable compounds, such as poly vinyl alcohol which exhibit the functional capacity to complex with the catalysts so as to deactivate them while not forming volatile polar by-products or residual unreacted compounds.

The process of the invention is also especially applicable to homogeneous solution polymerization which is also substantially adiabatic, that is to say the heat of polymerization is accommodated by a rise in temperature of the polymerization reactor contents, here principally solvent. This adiabatic process typically would have no internal cooling and suitably no external cooling. The reactor outlet stream removes the heat of polymerization from the reactor. The productivity of such adiabatic processes can be improved by cooling the inlet solvent and/or monomer stream(s) prior to introduction into the reactor to permit a greater polymerization exotherm. Thus the catalyst, cocatalyst and scavenger selections disclosed in this application can be advantageously practiced in a continuous, solution process operated at or above 140° C., above 150° C. or above 160° C., up to about 225° C. Most preferably the solution polymerization process for semi-crystalline polymers operated at a temperature from 140° C.–220° C. Typically this process is conducted in an inert hydrocarbon solvent, linear, cyclic or branched aliphatic, or aromatic, at a pressure of from 20 to 200 bar.

These catalysts' ability to provide a commercially desirable polymer at elevated temperatures contributes to a greater exothenn, to high polymer contents in the reactor because of lower viscosity, and to reduced energy consumption in evaporating and recycling solvent, and better monomer and comonomer conversions.

The α-olefins suitable for use in the preparation of the ethylene copolymers, or for the polyethylene copolymers, are preferably $C_3$ to $C_{20}$ α-olefins, but will include higher carbon number olefins such as polymerizable macromers having up to five hundred carbon atoms, or more. Illustrative non-limiting examples of such α-olefins are one or more of propylene, 1-butene, 1-pentene, 1-hexene, 1-octene, and 1-decene. Included in the term olefins for the purposes of describing effectively copolymerized monomers are the constrained-ring cyclic monoolefins such as cyclobutene, cyclopentene, norbornene, alkyl-substituted norbornes, alkenyl-substituted norbomenes, and the higher carbon number cyclic olefins known in the art, see U.S. Pat. No. 5,635,573, incorporated herein by reference for purposes of U.S. patent practice, and known copolymerizable diolefins, e.g., 1,4-hexadiene, ethylidene-norbornene, and vinyl-norbornene. Vinyl aromatic monomers, e.g., styrene and alkyl-substituted styrene monomers are additionally suitable. The polyethylene copolymers can range from semicrystalline to substantially amorphous; and will typically have a substantially random arrangement of at least the ethylene and the olefin comonomers. As will also be apparent to those skilled in the art, the use of asymmetrically substituted hafnium compounds of the invention enable the preparation of syndiotactic polymers from prochiral olefins, e.g., like propylene. Processes for such will also benefit from the increased productivity and molecular weights described here for ethylene copolymers.

The invention ethylene copolymer plastomers will preferably exhibit semi-crystalline characteristics, e.g., melting points ranging from about 85° C. to 115° C. The molecular weight (nunber-average molecular weight) of the plastomers of the invention will range from about 10,000 to about 60,000, preferably about 20,000 to about 50,000. The molecular weight for ethylene copolymer plastorners is more typically stated in terms of their polyethylene melt index (MI) (defined in ASTM 1238 190/2.16), those will typically range form 0.01 to 10.0, preferably 0.005 to 6.0, more preferably about 0.01 to less than 3.0. Ethylene copolymer elastomers will typically have $M_n \geq 60,000$ up to about 250,000, and can optionally comprise one or more non-conjugated or cyclic diolefin, in addition to ethylene and one or more a-olefin, typically propylene.

In terms of polymer density, the polymers capable of production in accordance the invention, can range from about 0.850 to about 0.930, preferably from 0.087 to 0.925, more preferably 0.089 to 0.920. The plastomers of the invention will contain about 60 to about 80 weight percent ethylene, preferably about 60 to 75 weight percent ethylene.

The catalyst complexes of the invention are also capable of significant comonomer incorporation, for example for ethylene with $C_3$–$C_8$ α-olefins and, optionally, $C_5$–$C_{20}$ non-conjugated diolefins, or with any of the other known monomers capable of copolymerization with ethylene, and are capable of high catalyst productivities and high molecular weight copolymers under industrially useful solution polymerization conditions. Such conditions are typically operated at ambient to medium high pressures (that is below about 500 bar) at temperatures ranging from about 40° C. to 140° C., where the polymerizable monomers are contacted with the catalyst complexes in an essentially liquid phase polymerization medium such as an aliphatic or aromatic solvent or diluent. The catalysts may be supported in accordance with known support methods for metallocene catalysts, particularly for use in slurry polymerization conditions. Both solution and slurry conditions are well known in the art and easily adapted for use with the catalysts according to this invention.

EXAMPLES

The following examples are presented to illustrate the foregoing discussion. All parts, proportions and percentages are by weight unless otherwise indicated. Although the examples may be directed to certain embodiments of the present invention, they are not to be viewed as limiting the invention in any specific respect. In Tables 1 and 2, "MCN" is an abbreviation for metallocene, particularly the hafnocenes of the invention, and "CC" is an abbreviation for co-catalyst.

High Temperature Semi-Batch Polymerization

Ethylene/1-octene copolymerizations were carried out in a well-stirred 1 L batch reactor equipped to perform coordination polymerization in the presence of an inert hydrocarbon (hexane) solvent at pressures up to 600 psig and temperatures up to 150° C. In the vapor-liquid (VL) polymerization system, the polymerization occurs in the liquid phase whereas ethylene was continuously fed to the reactor to keep the vapor phase overhead pressure constant at 265 psi during the polymerization. In those experiments, the reactor temperature was kept constant at 140° C. by throttling the amount of steam added to the reactor mantle and by adjusting the amount of catalyst fed to the reactor by the pump. Typically, 250 mL of dried hexane, 18 mL of dried 1-octene, and 1.0 mL of a 10 wt % triisobutylaluminum solution (toluene or hexane), a poisons scavenger, were fed to the reactor, which was then brought to 140° C. The reactor content was then pressurized with 265 psi ethylene by feeding ethylene and maintained at constant ethylene pressure throughout the polymerization. The polymerization was started by continuously feeding a pre-activated solution (toluene or hexane) of the catalyst during the polymerization. Pre-activation was accomplished by contacting the catalyst and co-catalyst in toluene prior to introduction into the reactor. The catalyst flow rate was stopped and the reactor was allowed to cool to room temperature and depressurized. The product was precipitated out of solution and then dried in a hood at room temperature overnight.

Example 1A

Preparation of 6-(p-tert-butylphenyl)-6'-(p-nbutylphenyl)-fulvene:

In a 1000 milliliter round bottom flask, 43.92 grams of the corresponding disubstituted benzophenone were dissolved in tetrahydrofuran (500 milliliters). To this solution was added 90.0 milliliters of sodium cyclopentadienide in tetrahydrofuran (Aldrich, 2.0 M). The reaction mixture was allowed to stir for 3 days in an inert atmosphere (glove box). The reaction mixture was then brought out of the box and poured in 300 milliliters of water. 400 milliliters of diethyl ether were added to the mixture. The organic layer was separated. The aqueous layer was extracted once with diethyl ether. The ether layers were combined and dried with magnesium sulfate for 4 hours. The magnesium sulfate was separated by filtration. A brick-red oil was obtained after the solvent was evaporated. The product was purified by column chromatography (silica gel, hexane). This gave 39.11 grams of 6-(p-tert-butylphenyl)-6'-(p-nbutylphenyl)-fulvene. The structure of the product was easily determined by the $^1$H NMR collected in CDCl$_3$ at room temperature. Small impurities are observed in the spectrum, but these impurities do not affect the subsequent reaction.

Example 1B

Preparation of 6-(p-tert-butylphenyl)-6'-(p-methylphenyl)-fulvene:

In a 100 milliliter round bottom flask, 5.13 grams of the appropriated disubstituted benzophenone were dissolved in tetrahydrofuran (50 milliliters). To this solution was added 10.0 milliliters of sodium cyclopentadienide in tetrahydrofuran (Aldrich, 2.0 M). The reaction mixture was allowed to stir for 3 days in an inert atmosphere (glove box). The reaction mixture was then brought out of the box and poured in 30 milliliters of water. 00 milliliters of diethyl ether were added to the mixture. The organic layer was separated. The aqueous layer was extracted once with diethyl ether. The ether layers were combined and dried with magnesium sulfate for 4 hours. The magnesium sulfate was separated by filtration. A brick-red oil similar to the compound described above was obtained after the solvent was evaporated. The product was purified by column chromatography (silica gel, methylenechloride:hexane::9:1). This gave 2.32 grams of 6-(p-tert-butylphenyl)-6'-( p-methylphenyl)-fulvene. The structure of the product was easily determined by the $^1$H NMR collected in CDCl$_3$ at room temperature. Small impurities are observed in the spectrum, but these impurities do not affect the subsequent reaction.

Example 2A

Preparation of (p-tBuPh)(p-nBuPh)C(Cp)(Flu)Li.

2.317 grams of lithium fluorenyl were suspended in 40 milliliters of toluene. To this suspension was added a solution containing 4.608 grams of 6-(p-tert-butylphenyl)-6'-(p-nbutylphenyl)-fulvene dissolved in approximately 80 milliliters oftoluene. The reaction is allowed to stir for 30 minutes. After removing the solvent and triturating with pentane, the solid product was collected by filtration and washed with pentane. This procedure afforded 6.17 grams of product. The identity of the product was established by $^1$H NMR in C$_6$D$_6$ at room temperature. The peaks in the aromatic region are broad but clearly defined and easily assigned.

Example 2B

Preparation of (p-tBuPh)(p-MePh)C(Cp)(Flu)Li.

1.192 Grams of lithium fluorenyl were suspended in 40 milliliters of toluene. To this suspension was added a solution containing 2.081 grams of 6-(p-tert-butylphenyl)-6'-(p-methylphenyl)-fulvene dissolved in approximately 80 milliliters oftoluene. The reaction is allowed to stir for 1 hour. After removing the solvent and triturating with pentane, the solid product was collected by filtration and washed with pentane. This procedure afforded 2.960 grams of product. The identity of the product was established by $^1$H NMR in C$^6$D$^6$ at room temperature. The peaks in the aromatic region are broad but clearly defined and easily assigned.

Example 3A

Preparation of (p-tBuPh)(p-nBuPh)C(Cp)(Flu)HfCl$_2$.

To a diethyl ether solution containing 5.45 grams of (p-tBuPh)(p-nBuPh)C(Cp)(Flu)Li was added 6.6 milliliters of n-BuLi (Aldrich, 1.6 M) The lithiation reaction was allowed to stir for 2.5 hours. To the dilithio salt was added 3.45 grams of HfCl$_4$ as a solid. The reaction mixture was stirred for 14 hours. The lithium chloride was separated by filtration. After evaporating the solvent, the product was extracted with dichloromethane to remove residual lithium chloride. The solvent was removed by evaporation. This left a dark oil. To the oil was added approximately 80 milliliters of pentane and 10 milliliter of diethyl ether. This caused a small amount of solids to precipitate. The mixture was allowed to sit in the refrigerator for 14 hours. This cooling caused more precipitation. The solid product was collected by filtration and dried under vacuum to afford 2.532 grams of an orange solid. Cooling the filtrate for another 4 hours gave a second crop of product (0.680 grams) for a collective yield of 3.212 grams. The identity of the product was established by $^1$H NMR in C$_6$D$_6$ at room temperature.

Example 3B

Preparation of (p-tBuPh)(p-MePh)C(Cp)(Flu)HfCl$_2$.

To a diethyl ether solution containing 2.96 grams of (p-tBuPh)()-nMePh)C(Cp)(Flu)Li was added 3.9 milliliters of n-BuLi (Aldrich, 1.6 M) The lithiation reaction was allowed to stir for 4 hours. To the dilithio salt was added 2.00 grams of HfCl$_4$. The reaction mixture was stirred for 14 hours. After evaporating the solvent, the product was extracted with dichloromethane to remove the lithium chloride. The solvent was removed by evaporation. This left a semisolid which was washed with pentane. The product was collected by filtration and rinse with a small amount of cold pentane to remove hydrocarbon impurities. This procedure provided 3.733 grams of an orange solid. The identity of the product was established by $^1$H NMR in C$_6$D$_6$ at room temperature.

Example 4A

Methylation of (p-tBuPh)(p-nBuPh)C(Cp)(Flu)HfCl$_2$.

Three equivalents of MeMgBr (Aldrich, 3.0 M in diethyl ether) were added to a cold suspension containing 3.63 grams of (p-tBuPh)(p-nBuPh)C(Cp)(Flu)HfCl$_2$ in toluene (−35° C.). The reaction was allowed to reach room temperature over 30 minutes. The reaction was then heated to 80° C. for two hours. The heating turns the reaction mixture dark brown. The reaction was filtered using celite to remove a dark solid. To the filtrate was added an excess of trimethylchlorosilnane and stirred for 2 hours. This last step ensures that the excess MeLi is quenched. The solvent is replaced by methylenedichloride, and the LiCl precipitate was separated by filtration. The volume is reduced to a minimum and pentane is added to induce precipitation. After cooling overnight the yellow product is collected by filtration. This procedure afforded 1.70 grams of a bright yellow solid. The identity of the product was established by $^1$H NMR in $C_6D_6$ at room temperature.

Example 4B

Methylation of (p-tBuPh)(p-MePh)C(Cp)(Flu)HfCl$_2$.

Three equivalents of MeMgBr (Aldrich, 3.0 M in diethyl ether) were added to a cold suspension containing 3.70 grams of (p-tBuPh)(Cp-MePh)C(Cp)(Flu)HfCl$_2$ in toluene (−35° C.). The reaction was allowed to reach room temperature over 30 minutes. The reaction was then heated to 80° C. for two hours. The reaction was filtered through celite to remove a dark solid. To the filtrate was added an excess of trimethylchlorosilnane and stirred for 3 hours. This last step ensures that the excess MeLi is quenched. The solvent is replaced by methylenedichloride, and the LiCl precipitate was separated by filtration. The volume is reduced to a minimum and pentane is added to induce precipitation. After cooling overnight the yellow product is collected by filtration. The identity of the product was established by $^1$H NMR in $C_6D_6$ at room temperature.

Example 5

Synthesis of (p-nBuPh)(p-tBuPh)C(Cp)(2,7-t-BuFlu)HfCl$_2$:

To an ether solution consisting of 1.35 grams of 6,6′-diphenylfulvene was added a solution consisting of 1.12 grams of lithium 2,7-di-tert-butylfluorene. After 20 minutes, a beige solid began to precipitate. The reaction was stirred for 6 hours. One equivalent of nBuLi (7.38 milliliters, 1.6M in diethyl ether, Aldrich) was added to the reaction. After 15 hours the reaction color changed to a burgundy-red and red a precipitate formed. To the red mixture was added 1.26 grams of hafniumtetrachloride. The reaction was allowed to stir for 3 hours. The mixture was orange-yellow with copious precipitate. The solvent was replaced with dichloromethane and filtered. It was necessary to wash the residual solids several times to extract more product. The solvent was removed under reduced pressure. The product was triturated with pentane and collected by filtration. This left an orange solid (1.045 grams).

Synthesis of (p-nBuPh)(p-tBuPh)C(Cp)(2,7-t-BuFlu)HfMe$_2$: To a cold solution (−35° C.) containing 1.00 grams of (p-nBuPh)(p-tBuPh)C(Cp)( 2,7-t-BuFlu)HfCl$_2$ in toluene was added three equivalents of MeMgBr (3.0 M, Aldrich). The reaction was allowed to reach room temperature slowly and then heated at 80° C. for 3 hours. This turned the reaction dark brown. The reaction was brought into the glovebox and passed through a celite pad. This allowed an orange solution to be collected. The solvent volume was reduced and the product triturated with pentane. The product was collected by filtration (0.300 grams).

Symbols for Tables 1-3 below:

| Catalyst ("Cat") | Metallocene ("MCN") Compound |
|---|---|
| A (Comparative) | Diphenylmethylene(cyclopentadienyl)(fluorenyl) hafnium dimethyl |
| B (Comparative) | (p-tert-butylphenyl)(p-methylphenyl)methylene (cyclopentadienyl)(fluorenyl) hafnium dimethyl |
| C | (p-tert-butylphenyl)(p-n-butylphenyl)methylene (cyclopentadienyl)(fluorenyl) hafnium dimethyl |
| D | (p-tert-butylphenyl)(p-n-butylphenyl)methylene (cyclopentadienyl)(2,7-di-tert-butylfluorenyl) hafnium dimethyl |
| E (Comparative) | di(p-tert-butylphenyl)methylene(cyclopentadienyl) (2,7-di-tert-butyl-fluorenyl) hafnium dimethyl |

| Activator ("Act") | Compound |
|---|---|
| I | [N,N-dimethylanilinium][tetrakis(pentafluorophenyl) borate] |

TABLE 1

| Cat/Act* | Yield (g) | Activity (g/mmol*min) | Wt % C8 | Mw | Mn | Mw/Mn |
|---|---|---|---|---|---|---|
| 1)A/I | 16.8 | 375 | 22.7 | 155562 | 60828 | 2.56 |
| 2)B/I | 17.8 | 147 | 20.8 | 181976 | 64125 | 2.84 |
| 3)C/I | 19.5 | 517 | 21.0 | 153617 | 16358 | 9.39 |
| 4)C/I | 10.9 | 743 | Nm | 340782 | 75466 | 4.52 |
| 5)C/I | 13.9 | 1037 | Nm | 187160 | 79822 | 2.34 |

*All polymerizations ran for 10 minutes, with the exception of B/I, which was 19 minutes. The symbol "nm" means not measured.

TABLE 2

| Cat/Act* | Yield (g) | Activity (g/mmol*min) | MI(dg/min) (ASTM D-1238(E) |
|---|---|---|---|
| 1)A/I | 16.8 | 375 | 0.041 |
| 6)D/I | 14.1 | 778 | 0.009 |
| 7)D/I | 19.0 | 715 | 0.012 |

*Polymerizations conducted as for Table 1.

TABLE 3

| Cat/Act* | Activity (g-polymer/ g-cat) | Wt % C8 | Mw | Mn | Mw/Mn |
|---|---|---|---|---|---|
| 8) A/I | 250 | 29.2 | 152.7 | 69.1 | 2.22 |
| 9)E/I$^2$ | 273 | 24.8 | 215.3 | 98.9 | 2.18 |

*notes: All polymerizations were conducted as done for Tables 1 and 2 above except that Table 3 reactions were stopped after 30 min. $^1$The values reported were the averages of 5 runs where the amount of MNC was varied between 10.5 and 20 mg. $^2$The values reported were the averages of 3 runs where the amount of MCN was varied between 5 and 10.5 mg.

As can been seen in Table 1, the invention catalysts of examples 3)–5) show significant improvement in actives, and to a lesser extent, improvements in weight-and number-average molecular weight where the bridge aryl-groups are substituted in accordance with the invention, as opposed to where not. The Mw/Mn measurement for 3) is suspect but the variance observed is not understood at this time. It is believed that a repeat under the conditions used would yield molecular weight values in line with 4) and 5). Table 2 illustrates a direct comparison for the MCN "A", with unsubstituted bridge aryl groups and unsubstituted fluorenyl groups, against MCN "D" having both bridge aryl group substitution and fluorenyl group substitution in accordance with the invention. Table 3 illustrates MCN "E" with alkyl substitution on the bridge aryl groups, that substitution not including the $C_3$ or greater linear n-alkyl of the invention, and substitution on fluorenyl group as for MCN "D" of the invention. It is apparent that the activities of 8) and 9) are comparable but with 9) showing improvement in molecular weights. Since 8) illustrates a standard for comparison with MCN "A", the same standard for Tables 1 and 2, "E" is expected to show similar activities to those exhibited by "A" and is inferior to "C" and "D" of the invention.

The following is claimed:

1. A polymerization process for prepareing ethylene copolymers having a density of 0.850–0.930 g/ml comprising contacting, under homogeneous polymerization conditions at a reaction temperature from 60° C. to 250° C., ethylene and one or more comonomers with a hafnocene catalyst complex derived from
   a) a biscyclopentadienyl hafnium organometallic compound having
      (i) at least one unsubstituted cyclopentadienyl ligand or aromatic fused-ring substituted cyclopentadienyl ligand,
      (ii) one aromatic fused-ring substituted cyclopentadienyl ligand,
      (iii) and a covalent bridge connecting the two cyclopentadienyl ligands, said bridge comprising a single carbon or silicon atom with two aryl groups, each aryl group substituted with either, a $C_1$–$C_{20}$ hydrocarbyl group at least one of which is a linear $C_3$ or greater substituting; and
   b) an activating cocatalyst compound.

2. The process of claim 1 wherein said activating cocatalyst compound comprises a halogenated tetraaryl-substituted Group 13 anion wherein at least one aryl substituent contains at least two cyclic aromatic rings.

3. The process of claim 1 wherein the aromatic fused-ring substituted cyclopentadienyl ligand of ii) is a substituted or unsubstituted fluorenyl ligand.

4. The process of claim 3 wherein said unsubstituted cyclopentadienyl ligand or aromatic fused-ring substituted cyclopentadienyl ligand is an unsubstituted cyclopentadienyl or indenyl ligand.

5. The process of claim 4 wherein said hafnium compound is selected from the group consisting of (p-tert-butylphenyl)(p-n-butylphenyl)methylene(cyclopentadienyl)(fluorenyl)hafnium dimethyl, (p-tert-butylphenyl) (p-n-butylphenyl)methylene(cyclopentadienyl)(2,7-dimethyl-9-fluorenyl) hafnium dimethyl, (p-tert-butylphenyl)(p-n-butylphenyl )methylene(cyclopentadienyl)(2,7-di-tert-butyl-9-fluorenyl) hafnium dimethyl, di(p-trimethylsilyl-phenyl)methylene(cyclopentadienyl) (fluorenyl) hafnium dimethyl, di(p-trimethylsilyl-phenyl)methylene (cyclopentadienyl)(2,7-dimethyl-9-fluorenyl) hafnium dimethyl and di(p-trimethylsilyl-phenyl)methylene (cyclopentadienyl)(2,7-di-tert-butyl-9-fluorenyl) hafnium dimethyl.

6. The process of claim 4 wherein said hafnium compound is covalently bridged between the biscyclopentadienyl ligands with a substituted silicon atom.

7. The process of claim 2 wherein the aryl substituent comprises at least one fused polycyclic aromatic ring.

8. The process of claim 7 wherein the fused polycyclic aromatic ring comprises a fluorine atom substitution for at least three ring-carbon hydrogen atoms.

9. The process of claim 8 wherein said halogenated tetraaryl Group 13 anion is [tetrakis(perfluoro-naphthyl)borate].

10. The process of claim 2 wherein the aryl groups of said halogenated tetraaryl Group 13 anion comprises at least one aromatic ring pendant in the 4 position to a phenyl ligand.

11. The process of claim 10 wherein said halogenated tetraaryl Group 13 anion is [tetrakis(perfluoro-4-biphenyl)borate].

12. The process of claim 8 wherein said cocatalyst precursor compound comprises an essentially cationic complex selected from substituted or unsubstituted anilinium, ammonium, carbenium and silylium cationic complexes.

13. The process of claim 9 wherein said cocatalyst precursor compound comprises a cationic complex selected from substituted or unsubstituted anilinium, ammonium, carbenium and silylium cationic complexes.

14. The process of claim 10 wherein said cocatalyst precursor compound comprises an essentially cationic complex selected from anilinium, ammonium, carbenium or silylium cationic complexes.

15. The process of claim 11 wherein said cocatalyst precursor compound comprises a cationic complex selected from anilinium, ammonium, carbenium or silylium cationic complexes.

16. The process of claim 1 wherein said homogeneous polymerization conditions are adiabatically conducted in a continuous polymerization process.

17. The process of claim 16 wherein the reaction temperature is in a range of 160° C. to 220° C.

18. The process of claim 17 wherein said homogeneous polymerization conditions are conducted in a continuous process at a pressure of at least 500 bar.

19. The process of claim 16 wherein said one or more comonomers are selected from the group consisting of propylene, 1-butene, 1-hexene, 1-octene, 1,4-hexadiene, ethylidene norbornene and vinyl norbornene.

20. The process of claim 18 wherein said one or more comonomers are selected from the group consisting of propylene, 1-butene, 1-hexene, and 1-octene.

* * * * *

UNITED STATES PATENT AND TRADEMARK OFFICE
CERTIFICATE OF CORRECTION

PATENT NO.   : 6,300,433 B1
DATED        : October 9, 2001
INVENTOR(S)  : George Rodriguez and Donna J. Crowther It is certified that error appears in the above-identified patent and that said Letters Patent is hereby corrected as shown below:

Column 10,
Line 58, please replace "140º C." with -- 140º C --.

Column 11,
Line 43, please replace " water. 00" with -- water. 100 --.

Column 12,
Line 17, please replace "$C^6D^6$" with -- $C_6D_6$ --.

Column 15,
Line 24, please replace "greater substituting" with -- greater substituent --

Signed and Sealed this

Twenty-fifth Day of June, 2002

*Attest:*

JAMES E. ROGAN
*Director of the United States Patent and Trademark Office*

*Attesting Officer*